United States Patent [19]

Towle

[11] Patent Number: 4,898,983

[45] Date of Patent: Feb. 6, 1990

[54] PREPARATION OF ARYL CARBONYL COMPOUNDS

[75] Inventor: Ian D. H. Towle, Cirencester, England

[73] Assignee: Raychem Limited, London, England

[21] Appl. No.: 270,401

[22] Filed: Nov. 7, 1988

Related U.S. Application Data

[63] Continuation of Ser. No. 96,416, Sep. 11, 1987, abandoned.

[30] Foreign Application Priority Data

Sep. 30, 1986 [GB] United Kingdom ............... 8623510

[51] Int. Cl.$^4$ ............................................. C07C 45/46
[52] U.S. Cl. .................................. 568/322; 568/319; 568/323
[58] Field of Search .......................... 568/319, 322, 323

[56] References Cited

U.S. PATENT DOCUMENTS

| 2,789,140 | 2/1957 | Von Glahn et al. | 568/319 |
| 3,769,349 | 10/1973 | Yukutomi et al. | 568/322 |
| 4,266,066 | 5/1981 | Spielmann et al. | 568/323 |
| 4,814,508 | 6/1989 | Gors et al. | 568/319 |

FOREIGN PATENT DOCUMENTS

| 0069598 | 7/1983 | European Pat. Off. | 568/319 |
| 178184 | 4/1986 | European Pat. Off. | 568/322 |
| 1110532 | 1/1956 | France | 568/319 |
| 747317 | 8/1970 | France | 568/322 |
| 2230615 | 10/1974 | France | 568/319 |
| 1434714 | 3/1976 | United Kingdom | 568/319 |
| 1420506 | 4/1976 | United Kingdom | 568/319 |

OTHER PUBLICATIONS

Troshina et al., Chem. Abst., vol. 98, #142607v (1983).
Lysenko et al., Chem. Abst., vol. 94, #110158f (1981).
Adeka Argus Chemical, Chem. Abs. 103:23805a (1985).
Effenberger et al., Ang. Chem. 84, 295–296 (1972).

*Primary Examiner*—James H. Reamer
*Attorney, Agent, or Firm*—Yuan Chao; Edith A. Rice; Herbert G. Burkard

[57] ABSTRACT

Friedel Crafts preparation of aryl carbonyl compounds having an exceptionally high degree of isomeric purity and freedom from by-products can be achieved by adding to the Lewis acid reaction system a protic controlling agent selected from ROX, water, RCOOX, RSO$_3$X, and ROY, wherein R is organic, X is hydrogen or metal, and Y is metal. Contrary to conventional expectation, the protic agent does not significantly alkylate or acylate the Friedel Crafts reaction product.

17 Claims, No Drawings

PREPARATION OF ARYL CARBONYL COMPOUNDS

This application is a continuation of application Ser. No. 096,416, filed Sept. 11, 1987, now abandoned.

This invention relates to the preparation of aryl carbonyl compounds, and in particular to para substituted aryl carbonyl compounds.

Aryl carbonyl compounds are useful in the preparation of poly(arylene ether ketones). In the preparation of these polymers it is essential that the monomers used be in a highly pure state to prevent undesirable side reaction. Furthermore, the polymers obtained should be stable enough to survive extrusion without undue deleterious effects on their physical properties. The substitution pattern of the monomers used can control the properties of the polymers synthesised, and it is generally recognized that the highest melting points and glass-rubber transition temperatures are obtained with all para linked polymers. Mixtures of substitution isomers are used when polymers of reduced crystallinity or lowered Tg are required, but the all para substituted polymers are most preferred. When mixtures of monomers are used, known ratios of the different isomers are needed, necessitating the use of pure starting materials. The present invention relates to a process for the preparation of aryl carbonyl compounds that improves outstandingly the degree of purity of the product and/or the degree of para substitution.

Aryl carbonyl compounds are also useful as chemicals and chemical intermediates, for example, in the pharmaceutical and agricultural chemicals, dyestuffs and general chemical additives area. Here too it is frequently found that the all para substituted carbonyl compounds are the most useful. Avoidance of concurrent formation of other isomeric by-products in the synthesis of such compounds is always beneficial economically and in some instances is essential because some isomeric compounds which are difficult to remove have been found to be toxic or even carcinogenic.

In a process described in Published European Pat. Application No. 0178184, Friedel-Crafts condensation of appropriate reactants is controlled to suppress side reactions including alkylation and/or ortho substitution by the addition of a controlling agent, such as a Lewis base, to the reaction medium.

One criterion for choosing the controlling agent in that process is that it should not be an acylating or alkylating agent, nor should it be acylatable under the reaction conditions. It is known that protic compounds act as acylating or alkylating agents in Friedel-Crafts reactions in the presence of aluminium trichloride.

However, it has now been surprisingly discovered that such compounds may be used as controlling agents in the process without themselves participating significantly in the acylation or alkylation reaction. It has also been discovered that water can be added as the controlling agent, contrary to the well-known requirement for substantially anhydrous conditions in Friedel-Crafts reactions.

Accordingly one aspect of the present invention provides a method of producing an aryl carbonyl compound which comprises reacting phosgene or a mono-, di-, or polyfunctional organic carboxylic acid, acid halide, alkyl ester or anyhdride together with an aromatic comonomer containing at least one activated hydrogen atom in a reaction medium comprising:

(A) a Lewis acid;
(B) a controlling agent comprising:
   (i) $R(OX)_a$ or added water which must be present in the reaction medium together with the Lewis acid before any reactant containing acid halide groups is added,
   (ii) $R(COOX)_a$,
   (iii) $R(SO_3X)_a$, or
   (iv) $(RO)_b Y$, which, if the Y—O linkages(s) are reactive to acid halide groups, must be present in the reaction medium together with the Lewis acid before any reactant containing acid halide groups is added,
   where R is a monovalent or polyvalent organic group compatible with the reactant(s) and the other components of the reaction medium,
   each X independently is a hydrogen atom or a monovalent metal atom,
   each a independently is 1 or 2,
   Y is a multivalent metal atom, and
   b is an integer equal to the valency of Y; and
(C) optionally a non-protic diluent;

the various components being present in such proportions and the reaction being conducted under such conditions that a para substituted carbonyl compound substantially free of by-products resulting from alkylation and/or ortho substitution is obtained.

Another aspect of this invention provides a process for the preparation of an aromatic carbonyl compound having the formula

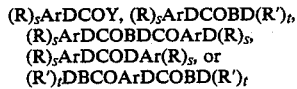

wherein each s and t are independently 1, 2 or 3 and each R, Ar, B, D and R' are independently as defined below, which process comprises reacting a first reactant, consisting of a substituted or unsubstituted aromatic compound containing at least one activated hydrogen atom of the formula

wherein Ar is a homo or hetero-aromatic mono, di or tri-cyclic moiety or a fused homo-aromatic condensed system containing less than 20 aromatic carbon atoms, or a hetero-aromatic system containing less than 8 nitrogen atoms, each R is as defined below and D is

wherein n, m, and p are each independently 0, 1, 2 or 3, provided that n+m+p is less than 4, and Z is —CO—, —SO$_2$—, —CO—C$_6$H$_4$—CO—, —O—(CF$_2$)$_q$—O— or V, provided that when n+m+p>0, any Ar group which contains an activated hydrogen atom is also linked to a V group, where V is a divalent radical of the formula

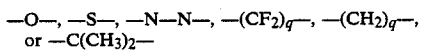

wherein q is 1 to 20;

with a second reactant, consisting of phosgene, or a mono-, di-, or polyfunctional organic carboxylic acid, acid halide, alkyl ester or anyhdride, or a mono-functional acyl compound of the general formula YCOBD(R')$_t$ or O(COBD(R')$_t$)$_2$
where t is 1, 2 or 3, or a di-functional acyl compound the general formula

YCOBDCOY wherein each B is independently a divalent substituted or unsubstituted aliphatic or cycloaliphatic group or Ar, and R and R' which may be the same or different are H, Br, Cl or F atom or a hydroxy, alkoxy, alkyl, aralkyl, unsubstituted or mono- or disubstituted amino, nitro, ester, acid, amide or imide group, and each Y represents a Br, Cl or F atom or a hydroxy or alkoxy group, subject to the proviso that any aromatic ring which contains an activated hydrogen atom also contains less than 2 alkoxy groups and to the further proviso that the aromatic carbonyl compound contains less than identical directly linked sequences containing at least one —SO$_2$— or —CO— in a reaction medium comprising:

(A) a Lewis acid in an amount of about one equivalent per equivalent of carbonyl groups or other basic species present in the reactant system plus about one equivalent per equivalent of controlling agent, plus an amount effective to act as a catalyst for the reaction;

(B) a controlling agent, in an amount from 0.1 to 4 equivalents per equivalent of acid halide groups present in the reactant system, comprising:
  (i) R(OX)$_a$ or added water which must be present in the reaction medium together with the Lewis acid before any reactant containing acid halide group is added,
  (ii) R(COOX)$_a$,
  (iii) R(SO$_3$X)$_a$, or
  (iv) (RO)$_b$ Y, which, if the Y—O linkage(s) are reactive to acid halide groups, must be present in the reaction medium together with the Lewis acid before any reactant containing acid halide groups is added,
    where R is an organic group compatible with the reactant(s) and the other components of the reaction medium,
    each X independently is a hydrogen atom or a monovalent metal atom,
    each a independently is 1 or 2,
    Y is a multivalent metal atom; and
    b is an integer equal to the valency of Y;
and
(C) a non-protic diluent in an amount from 0 to about 93% by weight, based on the weight of the total reaction mixture.

Pendant substituents which can be present on B or Ar groups include, for example lower alkyl, cyano, halogen, nitro, benzoyl or any other atom or group which will not interfere with the reaction by virtue of either its chemical nature or its location in the reactant from which the B group is derived.

The term "activated hydrogen atom" refers to a hydrogen atom displaceable under the electrophilic (Friedel-Crafts) reaction conditions employed in the reaction.

Preferred second reactants are phosgene, sulfuryl chloride and acyl compounds such as 4-fluorobenzoic acid halide, iso- or terephthalic acid halide, naphthalene 2,6-dicarboxylic acid halide, diphenyl ether 4,4'-dicarboxylic acid chloride and benzophenone 4,4'-dicarboxylic acid chloride.

Preferred combinations of substituted aromatic compounds and acyl compounds are fluorobenzene or diphenyl ether with 4-fluorobenzoyl chloride, acetyl chloride, acetic anhydride, iso- or terephthaloyl chloride, 4-hydroxybenzoyl chloride and 4-(4-hydroxy phenoxy)-benzoyl chloride.

In carrying out the process of this invention, equivalent amounts of the substituted aromatic compound and the aromatic acyl compound are preferably employed, although it may be advantageous in certain circumstances to use up to about a 2 molar excess of one reactant.

It will be readily understood that the group R in the controlling agent (B) is compatible with the reactant(s) and the other components of the reaction medium in the sense that it does not unacceptably interfere with the reaction. Provided that is so, R may be any desired monofunctional or (where appropriate) difunctional aliphatic aromatic or heterocyclic group, for example a substituted or unsubsituted alkyl, alkylene, aryl, arylene, alkaryl or aralkyl group. Simple aliphatic or aromatic groups are preferred, especially alkyl and alkylene groups, preferably n-alkyl and n-alkylene groups, and phenyl or naphthyl groups or phenylene or naphthylene groups.

Where the controlling agent is of the formula R(OX)$_a$ as defined above, the controlling agent may be an alcohol ROH, which also includes diols HOROH, or an organic metal oxide where X is, for example, an alkali metal such as sodium. In view of their strong affinity for reaction with acid halide groups, it is surprising that alcohols can be used as the controlling agent, even with the specified order of addition to the reaction mixture, which unexpectedly prevents reaction with the acid halide. Unbranched alcohols, e.g. n-alkanols, are preferred, especially the n-lower alkanols, e.g. n-butanol.

Where the controlling agent is of the formula R(COOX)$_a$ as defined above, this may be a carboxylic acid R—COOH, which includes dicarboxylic acids XOOC—R—COOX, or metal salts thereof where X is, for example an alkali metal.

Where the controlling agent is of the formula (R—O)$_b$ Y, Y is preferably a di— or trivalent metal atom and b is 2, 3 or 4 respectively e.g. (RO)$_3$Al, (RO)$_4$Ti, (RO)$_2$Zn.

Preferably R is a substituted or unsubstituted aryl group, or linear or branched C$_1$–C$_{20}$ alkyl group, or their arylene or alkylene equivalents where appropriate. More preferably R is an unsubstituted alkyl group especially a C$_1$–C$_5$ alkyl group, e.g. a methyl, ethyl, propyl, isopropyl, n-butyl or isobutyl group; or an unsubstituted aryl group, e.g. a phenyl or naphthyl group, and preferably aryl R groups are deactivated to electrophilic attack by attachment of electron-withdrawing groups.

The controlling agents may have fewer than 8 aliphatic carbon atoms, or even fewer than 5 aliphatic carbon atoms, directly bonded to one another, this including the possibilities that only one or no aliphatic carbon atoms are present, or that fewer than the stated numbers of such atoms are present in any one group, in the controlling agent molecule.

More specific examples of suitable controlling agents include methanol, ethanol, isopropanol, butanol, acetic acid, propionic acid, butanoic acid, trichloroacetic acid, trifluoroacetic acid, methane sulphonic acid, succinic acid, sodium methoxide, sodium ethoxide, $(CH_3CH_2O)_3Al$, $(CH_3COO)_3Al$, pentafluorophenol, and benzoic acid. It appears that trifluoroacetic acid may have the useful ability to produce a very fast reaction, or alternatively to reduce the amount of aluminum chloride needed for a given reaction speed possibly because the electron-withdrawing effect of the fluorine atoms produces a more highly activated aluminium atom in the resulting Lewis acid/controlling agent complex.

Mixtures of two or more controlling agents may be used if desired, and mixtures of the present protic controlling agent(s) with the non-protic Lewis base controlling agents described in the aforementioned European Patent Application No. 0178184 (whose disclosure is incorporated herein by reference) may be helpful. Methanol controlling agent plus sulpholane Lewis base is one example of such a mixture.

As mentioned above, the controlling agent acts, inter alia, to suppress undesirable side reactions, particularly ortho substitution of the aromatic rings in the reactant system. It is believed that the aromatic rings which are particularly susceptible to ortho substitution are active aryloxy groups. Such groups are referred to herein as undeactivated aryloxy groups. By "undeactivated aryloxy group" is meant an aryloxy group which is in a molecule in which there are no deactivating groups or is located at least two aromatic moieties (i.e. Ar as defined above) away from a deactivating group such as a carbonyl. Conversely a "deactivated aryloxy group" is an aryloxy group separated from a deactivating group, usually carbonyl, by an aromatic group containing one aromatic ring, fused aromatic rings or aromatic rings linked by direct bonds.

The amount of controlling agent present is preferably from 0.1 to 4 equivalents per equivalent of acid halide groups present in the reactant system. Amounts greater than 4 equivalents could be employed, if desired. However, no additional controlling effect is usually achieved by adding larger amounts. Thus, it is preferred to use no more than 4 equivalents, more preferably between 0.25 and 3 equivalents and especially between 0.5 and 2 equivalents per equivalent of acid halide groups. The actual amount of controlling agent added depends upon, inter alia, the particular controlling agent used, the nature of the reactants present and the type and amount of Lewis acid employed.

While it is not understood exactly how the controlling agent acts to control the reaction, it is believed that one or more of the following factors may be involved. It is thought that the controlling agent forms a complex or compound (hereinafter "complex" for simplicity) with the Lewis acid. The complex appears to act as a solvent for the product-Lewis acid complex formed during the reaction.

The term "Lewis acid" is used herein to refer to a substance which can accept an unshared electron pair from another molecule. Lewis acids which can be used in the practice of this invention include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. The use of substantially anhydrous aluminum trichloride as the Lewis acid is preferred.

The amount of Lewis acid used in the practice of this invention varies depending on the particular reactants and reaction medium selected. In all instances at least about one equivalent of Lewis acid per equivalent of carbonyl groups present in the reactant system is used plus one equivalent per equivalent of controlling agent used plus an amount effective to act as a catalyst for the reaction (also referred to herein as a catalytic amount). Generally a catalytic amount added is from about 0.05 to about 0.5 equivalents of Lewis acid per equivalent of acid halide in the reaction mixture. When aluminium chloride is used as the Lewis acid one equivalent is considered to be $AlCl_3$. Further, if a coreactant containing other basic species, such as sulfone groups, is used, additional Lewis acid may be required.

A non-protic diluent can also be employed, if desired, "non-protic" meaning that the diluent has no hydrogens directly bonded to oxygen or nitrogen. Such diluents are also known as "aprotic". Advantageously, the diluent should dissolve the aforementioned Lewis acid/controlling agent complex and resulting product/Lewis acid complex. It should also be relatively inert toward Friedel-Crafts reactions. The diluent is preferably somewhat polar as measured by its dielectric constant and solubility parameter. Preferably the dielectric constant of the diluent is at least about 2.0 at 24° C., and preferably in the range of from about 4.0 to about 25 at 24° C. The Hildebrand solubility parameter of the diluent is preferably at least about 7.2 $[cal/cm^3]^{\frac{1}{2}}$ and is preferably in the range of from about 9.2 to about 15 $[cal/cm^3]^{\frac{1}{2}}$. Preferred diluents include, for example, methylene chloride, carbon disulfide, o-dichlorobenzene, 1,2,4-trichlorobenzene, o-difluorobenzene, 1,2-dichloroethane, cyclohexane, 1,1,2,2,-tetrachloroethane and mixtures thereof.

The diluent is used in an amount from 0 to about 93% by weight, based on the weight of the total reaction mixture. The reactions can be run without the presence of a diluent. Typically the diluent is used in an amount of at least about 10%, preferably at least about 20% by weight of the reaction mixtures.

The term polynuclear aromatic moieties is used to mean aromatic moieties containing at least two aromatic rings. The rings can be fused, joined by a direct bond or by a linking group. In certain reactants, at least two of the aromatic rings are linked by an ether oxygen linkage. Other linking groups which can join aromatic rings in the aromatic moieties include for example, ether, carbonyl, sulphone, sulphide, amide, imide, azo, alkylene, perfluoroalkylene and the like.

The phenylene and polynuclear aromatic moieties contained in the reactants can contain substitutents on the aromatic rings. Such substitutents should not inhibit or otherwise interfere with the polymerisation reaction to any significant extent. Such acceptable substitutents include, for example, phenyl, halogen, ester, nitro, cyano, alkyl and the like.

Where an aromatic acid halide is employed, it is preferably a chloride or bromide. Examples of suitable acid halide reactants, aromatic coreactants which can be used with such acid halide reactants, and self-reacting acid halide reactants are described in the aforementioned European Published Pat. Application No. 0178184, the disclosure of which is incorporated herein by reference.

It is to be understood that combinations of reactants can be employed. For example, one or more acid halides can be used with one or more aromatic coreactants as long as the correct stoichiometry is maintained. Further, one or more acid halides can be included.

The temperature at which the reaction is conducted can be from about −50° C. to about +150° C. It is preferred to start the reaction at lower temperatures, for example at about −50° C. to about −10° C. particularly if the reactant system contains highly reactive reactants. After reaction has commenced, the temperature can be raised if desired, for example, to increase the rate of reaction. It is generally preferred to carry out the reaction at temperatures in the range of between about −30° C. and +25° C.

Since Lewis acid is present in the reaction medium as the catalyst for the Friedel-Crafts reaction, the resulting product contains Lewis acid complexed to the carbonyl groups.

Decomplexation can be accomplished by treating the polymerisation reaction mixture with a decomplexing base after completion of polymerisation. The base can be added to the reaction medium or the reaction medium can be added to the base. The decomplexing base must be at least as basic towards the Lewis acid as the basic groups on the product. Such decomplexation should preferably be effected before isolation of the product from the reaction mixture.

The amount of decomplexing base used should be in excess of the total amount of bound (complexed) and unbound Lewis acid present in the reaction mixture and is preferably at least twice the total amount of Lewis acid. Typical decomplexing bases which can be used include water, dilute aqueous hydrochloric acid, methanol, ethanol, acetone, N,N-dimethyl-formamide, N,N-dimethylacetamide, pyridine, dimethyl ether, diethyl ether, tetrahydrofuran, trimethylamine hydrochloride, dimethyl sulfide, tetramethylenesulfone, benzophenone, tetramethylammonium chloride, isopropanol and the like. The decomplexed product can then be removed by conventional techniques such as adding a nonsolvent for the product which is a solvent for or miscible with the Lewis acid/controlling agent complex and Lewis acid; spraying the reaction medium into a nonsolvent for the product; separating the product by filtration; or evaporating the volatiles from the reaction medium and then washing with an appropriate solvent to remove any remaining complex and diluent from the product.

This invention is further illustrated by the following examples, the formulae of all the respective product compounds being shown after Example 12.

EXAMPLE 1

Into a 250 ml flask equipped with a magnetic stirrer and nitrogen inlet was charged 75 mls of dichloromethane which was cooled to −25° C. To the cooled solvent was added 12.00 g (0.09M) of anhydrous aluminium chloride followed by 2.8 g (0.0378M) of butanol, the butanol being added at a rate such that the temperature in the reaction flask did not rise above −15° C. Finally 3.22 g (0.0189M) of diphenyl ether followed by 6 g (0.0378M) of p-fluorobenzoyl chloride were added and washed in the flask with 15 mls each of dichloromethane. Again the rate of addition was such that the temperature in the flask did not rise above −15° C. After all the components had been added the reaction mixture was allowed to warm slowly (over 2 hrs) to room temperature and maintained there for 6 hrs. The reaction mixture was de-complexed into 500 mls of cold (−18° C.) methanol giving a white solid which was collected by filtration. After drying the crude yield of 4,4′-bis(4-fluorobenzoyl) di phenyl ether was 94%. The solid was recrystallised from isobutylmethylketone giving the all para- isomer in 85% yield. The structure was confirmed by $^{13}$C and $'$H n.m.r spectroscopy.

A similar result was obtained using 4.61 g (0.0378M) of benzoic acid in place of the butanol. The crude yield of 4,4′-bis(4-fluorobenzoyl)diphenylether was 98% which after recrystallising from isobutylmethylketone gave an 86% yield of the pure isomer.

EXAMPLE 2

Following the procedure outlined in Example 1 4,4′-diphenoxybenzophenone was prepared using the reagents specified below.

| Anhydrous aluminium chloride | 7 g (0.0525 M) |
| --- | --- |
| n-Butanol | 1.6 g (0.0215 M) |
| Diphenyl ether | 7.32 g (0.043 M) |
| 4-Phenoxybenzoyl chloride | 5 g (0.0215 M) |

After recrystallising from isobutylmethylketone pure 4,4′-diphenoxybenzophenone was isolated in 84% yield, the structure being confirmed by $^{13}$C and $'$H n.m.r spectroscopy.

A similar result was obtained using 2.62 g (0.0215M) of benzoic acid in place of butanol. The pure product was isolated in 85% yield.

EXAMPLE 3

Following the procedure outlined in Example 1 1,3-bis(4-phenoxybenzoyl)benzene was prepared using the reagents specified below.

| Anhydrous aluminium chloride | 15.7 g (0.1181 M) |
| --- | --- |
| n-Butanol | 3.64 g (0.0492 M) |
| Diphenyl ether | 16.76 g (0.0984 M) |
| Benzene-1,3-di(carboxylic acid chloride) | 5 g (0.0246 M) |

After recrystallising from a mixture of methanol and toluene (3:1) pure 1,3-bis(4-phenoxybenzoyl)benzene was isolated in 83% yield, the structure being confirmed by $^{13}$C and $'$H n.m.r. spectroscopy.

A similar result was obtained using 6 g (0.0492M) of benzoic acid in place of butanol. The pure product was isolated in 85% yield.

EXAMPLE 4

Following the procedure outlined in Example 1 the compound (Ph-p-phenylene)

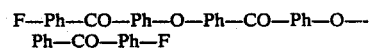
Ph—CO—Ph—F was prepared using the reagents specified below.

| Anhydrous aluminium chloride | 12.63 g (0.0947 M) |
| --- | --- |
| n-Butanol | 2.33 g (0.0315 M) |
| 4,4′-diphenoxybenzophenone | 5.77 g (0.0157 M) |
| 4-fluorobenzoylchloride | 5 g (0.0315 M) |

After recrystallising from 1,2-dichlorobenzene the pure material was isolated in 88% yield, the structure, above, being confirmed by $^{13}$C and $'$H n.m.r. spectroscopy.

A similar result was obtained using 3.84 g (0.0315M) of benzoic acid in place of butanol. The pure product was isolated in 92% yield.

EXAMPLE 5

Following the procedure outlined in Example 1 1,4-bis(4'-fluorobenzoyl)benzene was prepared using the reagents specified below.

| Anhydrous aluminium chloride | 16.63 g (0.125 M) |
|---|---|
| n-Butanol | 3.85 g (0.052 M) |
| Fluorobenzene | 5 g (0.0521 M) |
| Benzene-1,4-di(carboxylic acid chloride) | 5.2 g (0.026 M) |

After recrystallising from isobutylmethylketone pure 1,4-bis(4'-fluorobenzoyl) benzene was isolated in 83% yield, the structure was confirmed by $^{13}C$ and 'H n.m.r. spectroscopy.

A similar result was obtained using 6.34 g (0.052M) of benzoic acid in place of butanol. The pure product was isolated in 82% yield.

EXAMPLE 6

Following the procedure outlined in Example 1 4,4'-bis(4-fluorobenzoyl)biphenyl was prepared using the reagents specified below.

| Anhydrous aluminium chloride | 23 g 0.173 M |
|---|---|
| n-Butanol | 5.26 g 0.071 M |
| Fluorobenzene | 8.75 g 0.091 M |
| 4,4'-Biphenyl dicarboxylic acid dichloride | 10 g 0.036 M |

After crystallising from chlorobenzene pure 4,4'-bis(4-fluorobenzoyl)biphenyl was isolated in 88% yield, the structure was confirmed by $^{13}C$ and 'H n.m.r. spectroscopy.

EXAMPLE 7

Following the procedure outlined in Example 1 4,4'-bis(4-phenoxybenzoyl)biphenyl was prepared using the reagents specified below.

| Anhydrous aluminium chloride | 30.67 g 0.23 M |
|---|---|
| n-Butanol | 8 g 0.108 M |
| Diphenylether | 24.5 g 0.144 M |
| 4,4'-Biphenyl dicarboxylic acid dichloride | 10 g 0.036 M |

After crystallising from chlorobenzene pure 4,4'-bis(4-phenoxybenzoyl)biphenyl was isolated in 90% yield, the structure was confirmed by $^{13}C$ and 'H n.m.r. spectroscopy.

EXAMPLE 8

Following the procedure outlined in Example 1, but stirring the reaction mixture overnight, 4,4'-bis(4-fluorobenzoyl)-p-terphenyl was prepared using the reagents specified below.

| Anhydrous aluminium chloride | 62.4 g 0.483 M |
|---|---|
| n-Butanol | 19.24 g 0.26 M |
| p-Terphenyl | 15 g 0.065 M |
| 4-Fluorobenzoyl chloride | 20.65 g 0.13 M |

After crystallising from chlorobenzene/o-dichlorobenzene pure 4,4'-bis(4-fluorobenzoyl)-p-terphenyl was isolated in 88% yield, the structure was confirmed by $^{13}C$ and 'H n.m.r. spectroscopy.

The corresponding 4-chlorobenzoyl derivative was similarly prepared by substituting 4-chlorobenzoyl chloride for the 4-fluorobenzoyl chloride used in the above example.

EXAMPLE 9

Following the procedure outlined in Example 1 4-phenoxy-4'-fluorobenzophenone was prepared using the reagents specified below.

| Anhydrous aluminium chloride | 84 g 0.63 M |
|---|---|
| Propionic acid | 9.33 g 0.126 M |
| Diphenyl ether | 64.34 g 0.378 M |
| 4-Fluorobenzoyl chloride | 20 g 0.126 M |

After crystallising from methanol pure 4-phenoxy-4'-fluorobenzophenone was isolated in 89% yield, the structure was confirmed by $^{13}C$ and 'H n.m.r. spectroscopy.

EXAMPLE 10

Following the procedure outlined in Example 1 4-fluoro-4'-(4-fluorobenzoyl)biphenyl was prepared using the reagents specified below.

| Anhydrous aluminium chloride | 30.67 g 0.23 M |
|---|---|
| n-Butanol | 6.66 g 0.09 M |
| 4-Fluorobiphenyl | 15 g 0.087 M |
| 4-Fluorobenzoyl chloride | 14.27 g 0.09 M |

After crystallising from isobutylmethylketone pure 4-fluro-4'-(4-fluorobenzoyl)biphenyl was isolated in 84% yield, the structure was confirmed by $^{13}C$ and 'H n.m.r. spectroscopy.

EXAMPLE 11

Following the procedure outlined in Example 1 2,6-bis(4-fluorobenzoyl)naphthalene was prepared using the reagents specified below.

| Anhydrous aluminium chloride | 70.67 g 0.53 M |
|---|---|
| n-Butanol | 16.28 g 0.22 M |
| Naphthalene-2,6-dicarboxylic acid dichloride | 28 g 0.1107 M |
| 4-Fluorobenzene | 21.27 g 0.2213 M |

After crystallising from chlorobenzene pure 2,6-bis(4-fluorobenzoyl)napththalene was isolated in 90% yield, the structure was confirmed by $^{13}C$ and 'H n.m.r. spectroscopy.

EXAMPLE 12

Following the procedure outlined in Example 1 1,2-bis(4-phenoxybenzoyl)ethane was prepared using the reagents specified below.

| Anhydrous aluminium chloride | 106 g 0.795 M |
|---|---|
| n-Butanol | 14.8 g 0.199 M |
| Diphenyl ether | 130 g 0.764 M |
| Succinyl chloride | 30 g 0.194 M |

After crystallising from toluene pure 1,2-bis(4-phenoxybenzoyl)ethane was isolated in 91% yield, the structure was confirmed by $^{13}C$ and 'H n.m.r. spectroscopy.

The compound produced by Examples 1 to 12 respectively had the following structures (Ph=p-phenylene), those marked * being thought to be novel:

1. F—Ph—CO—Ph—O—Ph—CO—Ph—F

2. Ph—O—Ph—CO—Ph—O—Ph

3. Ph—O—Ph—CO—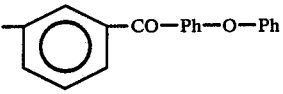—CO—Ph—O—Ph

4.* F—Ph—CO—Ph—O—Ph—CO—Ph—O—Ph—CO—Ph—F

5. F—Ph—CO—Ph—CO—Ph—F

6. F—Ph—CO—Ph—Ph—CO—Ph—F

7.* Ph—O—Ph—CO—Ph—Ph—CO—Ph—O—Ph

8.** F—Ph—CO—Ph—Ph—Ph—CO—Ph—F

Cl—Ph—CO—Ph—Ph—Ph—CO—Ph—Cl

9. Ph—O—Ph—CO—Ph—F

10.* F—Ph—Ph—CO—Ph—F

11. F—Ph CO—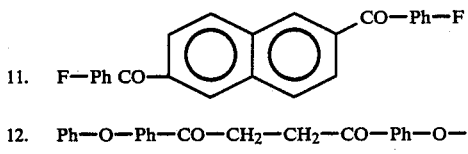—CO—Ph—F

12. Ph—O—Ph—CO—CH$_2$—CH$_2$—CO—Ph—O—Ph

I claim:

1. A method of preparing an aryl carbonyl compound which comprises reacting phosgene or a mono-, di-, or polyfunctional organic carboxylic acid, acid halide, alkyl ester or anhydride together with an aromatic co-monomer containing at least one activated hydrogen atom in a reaction medium comprising:
(A) a Lewis acid;
(B) a controlling agent comprising:
  (i) R(OX)$_a$ which must be present in the reaction medium together with the Lewis acid before any reactant containing acid halide groups is added,
  (ii) R(COOX)$_a$, or
  (iii) (RO)$_b$Y, which, if the Y—O linkage(s) are reactive to acid halide groups, must be present in the reaction medium together with the Lewis acid before any reactant containing acid halide groups is added,
  where R is a monovalent or polyvalent organic group compatible with the reactant(s) and the other components of the reaction medium,
  each X independently is a hydrogen atom or a monovalent metal atom,
  each a independently is 1 or 2,
  Y is a multivalent metal atom, and
  b is an integer equal to the valency of Y; and
(C) optionally a non-protic diluent;
the various component being present in such proportions and the reaction being conducted under such conditions that a para substituted carbonyl compound substantially free of by-products resulting from alkylation and/or ortho substitution is obtained.

2. A process for the preparation of an aromatic carbonyl compound having the formula (R)$_s$ArDCOY, (R)$_s$ArDCOBD(R')$_t$,
(R)$_s$ArDCOBDArD(R)$_s$, (R)$_s$ArDCODAr(R)$_s$, or
(R)$_t$DBCOArDCOBD(R')$_t$ wherein each s and t are independently 1,2, or 3 and each R, Ar, B, D and R, are independently as defined below, which process comprises reacting a first reactant, consisting of a substituted or unsubstituted aromatic compound containing at least one activated hydrogen atom of the formula (R)$_s$ArDH wherein Ar is a homo or hetero-aromatic mono, di, or tri-cyclic moiety or a fused homo-aromatic condensed system containing less than 20 aromatic carbon atoms, or a hetero-aromatic system containing less than 8 nitrogen atoms, each R is as defined below and D is —(ZAr)$_n$—(ZAr)$_m$—(ZAr)$_p$— wherein n, m, and p are each independently 0,1,2 or 3, provided that n+m+p is less than 4, and z is —CO—, —SO$_2$—, —CO—C$_6$H$_4$—CO—, —O—(CF$_2$)$_q$—O— or V, provided that when n+m+p>0, any Ar group which contains an activated hydrogen atom is also linked to a V group, where V is a divalent radical of the formula —O—, —S—, —N=N—, —(CF$_2$)$_q$—, —(CH$_2$)$_q$—, or —C(CH$_3$)$_2$ wherein q is 1 to 20; with a second reactant, consisting of phosgene, or a mono-, di- or polyfunctional organic carboxylic acid, acid halide, alkyl ester, or anhydride, or a monofunctional acyl compound of the general formula YCOBD(R')$_t$ or O(COBD(R')$_t$)$_2$ where t is 1, 2, or 3, or a difunctional acyl compound of the general formula

YCOBDCOY wherein each B is independently a divalent substituted or unsubstituted aliphatic or cycloaliphatic group or Ar, and R and R' which may be the same or different are a H, Br, Cl, or F atom or hydroxy, alkoxy, alkyl, aralkyl, unsubstituted or mono- or disubstituted amino, nitro, ester, acid, amide or imide group, and each Y represents a Br, Cl, or F atom or a hydroxy or alkoxy group, subject to the proviso that any aromatic ring which contains an activated hydrogen atom also contains less than 2 alkoxy groups and to the further proviso that the aromatic carbonyl compound contains less than 2 identical directly linked sequences containing at least one $-SO_2-$ or $-CO-$ in a reaction medium comprising:

(A) A Lewis acid in an amount of about one equivalent per equivalent of carbonyl groups or other basic species present in the reactant system plus about one equivalent per equivalent of controlling agent, plus an amount effective to act as a catalyst for the reaction;

(B) a controlling agent, in an amount from 0.1 to 4 equivalents per equivalent of acid halide groups present in the reactant system, comprising:
  (i) $R(OX)_a$ which must be present in the reaction medium together with the Lewis acid before any reactant containing acid halide groups is added,
  (ii) $R(COOX)_a$, or
  (iii) $(RO)_bY$, which, if the Y—O linkage(s) are reactive to acid halide groups, must be present in the reaction medium together with the Lewis acid before any reactant containing acid halide groups is added,
    where R is a monovalent or polyvalent organic group compatible with the reactant(s) and the other components of the reaction medium,
    each X independently is a hydrogen atom or a monovalent metal atom,
    each a independently is 1 or 2,
    Y is a multivalent metal atom, and
    b is an integer equal to the valency of Y; and (C) a non-protic diluent is an amount from 0 to about 93% by weight, based on the weight of the total reaction mixture.

3. A method according to claim 1 or 2 wherein the controlling agent is an alcohol, carboxylic acid or organic metal oxide.

4. A method according to claim 1 or 2, wherein R is an alkyl group.

5. A method according to claim 1 or 2, wherein the controlling agent is an n-alkanol.

6. A method according to claim 1 or 2, wherein R is an aryl group.

7. A method according to claim 1 or 2, wherein the controlling agent is an aryl carboxylic acid.

8. A method according to claim 1 or 2, wherein the controlling agent molecule contains fewer than 8 aliphatic carbon atoms directly bonded to one another.

9. A method according to claim 1 or 2, wherein the amount of controlling agent present in the reaction medium is between 0.1 and 4 equivalents per equivalent of acid halide groups present in the reactant system.

10. A method according to claim 1 or 2, wherein the Lewis acid is selected from aluminium trichloride, boron trichloride, aluminium tribromide, titanium tetrachloride, antimony pentachloride, ferric chloride, gallium trichloiide, and molybdenum penta-chloride.

11. A method according to claim 1 or 2, wherein the Lewis acid is aluminium trichloride.

12. A method according to claim 1 or 2, wherein the reaction is carried out in the presence of a non-protic diluent.

13. A method according to claim 1 or 2, wherein the reaction is carried out in the presence of a non-protic diluent having a dielectric constant of at least 2.0 at 24° C.

14. A method according to claim 1 or 2, wherein the reactant system comprises p-phenoxybenzoyl chloride, and diphenyl ether.

15. A method according to claim 1 or 2, wherein the reactant system comprises diphenyl ether and terephthaloyl chloride.

16. A method according to claim 1 or 2, wherein the reactant system comprises diphenyl ether and acetic anhydride and the resulting monomer is converted to p-phenoxybenzoyl chloride or bromide.

17. A method according to claim 1 or 2, wherein the reaction is conducted at a temperature in the range from −30° C. to +25° C.

* * * * *